United States Patent [19]

Hulkenberg et al.

[11] Patent Number: 5,409,940
[45] Date of Patent: Apr. 25, 1995

[54] 3,4-DEHYDROPIPERIDINE DERIVATIVES

[75] Inventors: Antonius Hulkenberg; Karin J. van Charldorp; Rolf van Hes; Ineke van Wijngaarden, all of Weesp, Netherlands

[73] Assignee: Duphar International Research B.V., Weesp, Netherlands

[21] Appl. No.: 137,753

[22] Filed: Oct. 19, 1993

Related U.S. Application Data

[63] Continuation of Ser. No. 911,630, Jul. 10, 1992, abandoned.

[30] Foreign Application Priority Data

Jul. 15, 1991 [EP] European Pat. Off. ............ 91201855

[51] Int. Cl.$^6$ .................... C07D 409/04; A61K 31/44
[52] U.S. Cl. ........................... 514/337; 546/274
[58] Field of Search ................... 546/274; 514/337

[56]  References Cited

U.S. PATENT DOCUMENTS 4,259,338  3/1981  Paioni et al. ...................... 546/269

FOREIGN PATENT DOCUMENTS 0021924  1/1981  European Pat. Off. .
0303507  2/1989  European Pat. Off. .
0398413  11/1990  European Pat. Off. .
2056435  3/1981  United Kingdom .

OTHER PUBLICATIONS

Paloni et al. CA 93: 132373d, 1980.
Clark et al. Principles of Psychopharmacology Academic Press, N.Y. London, 1970, pp. 166–167.

*Primary Examiner*—Jane T. Fan
*Attorney, Agent, or Firm*—Stevens, Davis, Miller & Mosher

[57]  ABSTRACT

The invention relates to a group of new 3,4-dehydropiperidine derivatives of the formula

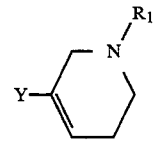

wherein
$R_1$ is a hydrogen atom or an alkyl group having 1–3 carbon atoms;
Y is a group of the general formula 2

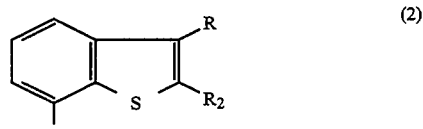

wherein
$R_2$ is a group of the formula $-(CH_2)_n-C(=X)-NR_3R_4$, $-(CH_2)_n-SO_2-NR_3R_4$, $-(CH_2)_n-NR_5-C(=X)-R_6$ or $-(CH_2)_n-NR_5-SO_2-R_6$, wherein $R_3$, $R_4$ and $R_5$ independent of each other represent hydrogen or alkyl (1–3C), $R_6$ is alkyl (1–3C), X represents O or S; n is 0–4, and R is hydrogen or alkyl (1–3C).

These compounds have interesting serotonin-1-like (partial) agonistic activity and can be used for the treatment of migraine.

3 Claims, No Drawings

3,4-DEHYDROPIPERIDINE DERIVATIVES

This application is a continuation of application Ser. No. 07/911,630, filed Jul. 10, 1992 now abandoned.

The invention relates to new 3-substituted 3,4-dehydropiperidine derivatives having anti-migraine activity.

It was found that 3,4-dehydropiperidine derivatives of the general formula 1

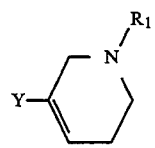

(1)

wherein
$R_1$, is a hydrogen atom or an alkyl group having 1–3 carbon atoms;
Y is a group of the general formula 2

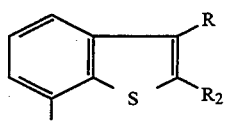

(2)

wherein
$R_2$ is a group of the formula —$(CH_2)_n$—C(=X)—$NR_3R_4$, —$(CH_2)_n$—$SO_2$—$NR_3R_4$, —$(CH_2)_n$—$NR_5$—C(=X)—$R_6$ or —$(CH_2)_n$—$NR_5$—$SO_2$—$R_6$, wherein $R_3$, $R_4$ and $R_5$ independent of each other represent hydrogen or alkyl (1–3C), $R_6$ is alkyl (1–3C), X represents O or S; and n is 0–4; R is hydrogen or alkyl (1–3C),
have serotin 1-like (partial) agonistic activity which can be used for the treatment of migraine.

The so-called prodrugs and acid addition salts of the compounds of formula 1 also belong to the invention. Prodrugs are to be understood to mean derivatives of these compounds, which are inactive as such but from which, after removal of an easily removable group, i.e. an ester group or an ether group, an active compound of formula 1 is obtained.

When a chiral center is present both the different enantiomers and the racemate belong to the invention.

Examples of suitable acids with which the compounds according to the invention can form pharmaceutically acceptable salts are hydrochloric acid, sulphuric acid, phosphoric acid, nitric acid, organic acids, like citric acid, fumaric acid, tartaric acid, acetic acid, maleic acid, benzoic acid, p-toluene sulphonic acid, methane sulphonic acid and the like.

The compounds of the invention show an interesting serotonin 1-like (partial) agonistic activity. Compounds having this activity are potential antimigraine drugs.

This activity against migraine is determined by means of the following test model. Serotonin causes via stimulation of 5-HT$_1$-like receptors a concentration-dependent contraction of isolated strips of A. basilaris of the pig. (Naunyn Schmiedeberg's Arch. of Pharmacol. 1990, suppl to vol. 341, R 89). The compounds according to the invention are active in dosages which as a rule are between 0.1 and 100 mg/kg after oral administration.

The compounds can be brought into a form suitable for humane application in the conventional manner, that is to say, formulated to compositions suitable for this purpose and to be preferable administered orally.

The new compounds according to the invention can be obtained in a manner known for the synthesis of analogous compounds.

Compounds having formula (1) wherein $R_1$ has the above meanings and Y is a group of formula 3

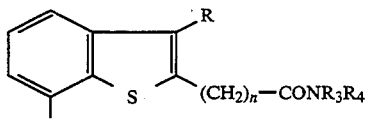

(3)

wherein n, R, $R_3$ and $R_4$ have the above meanings can be obtained, for example, by reacting a compound of formula 4

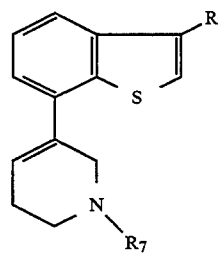

(4)

wherein $R_7$ is alkyl(1–3C) or benzyl with butyllithium, followed a) by a reaction with $CO_2$, and conversion of the carboxylate so-obtained into an amide, or b) by a reaction with an alkylisocyanate, or c) by alkylation with a suitable functionalised bromoalkylderivative.

Compounds having formula 1 wherein $R_1$ has the above meanings and Y is a group having formula 5

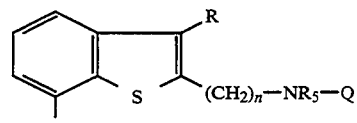

(5)

wherein n, R and $R_5$ have the above meanings, and Q is a group of the formula —(C=X)—$R_6$ or —$SO_2$—$R_6$, in which groups X, and $R_6$ have the above meanings, can be prepared by reduction of a compound obtained according to a), b) or c) above, with LiAlH$_4$ giving the corresponding amines, followed by reaction with a suitable acylating or sulfonylating agent.

Compounds of the formula 1 wherein $R_1$ has the above meanings and Y is a group of formula 6

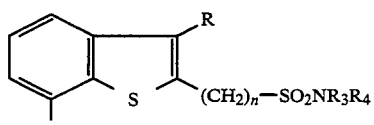

(6)

wherein n, R, $R_3$ and $R_4$ has the meaning given above, can be prepared from the corresponding lithium sulfinate of the formula 7

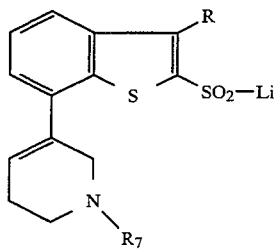

wherein R has the meaning given above, $R_7$ is alkyl(1-3C) or benzyl according to methods described in Synthesis, (1986), 1031; Synthesis, (1986), 852, and Bull. Chem. Soc. Jpn, 43, (1970), 1256.

To obtain the final compounds according to these methods wherein $R_1$ is hydrogen, the protective benzyl group has to be removed by methods known for debenzylation.

The invention will now be described in greater detail with references to the ensuing specific examples.

EXAMPLE I 2-(N-methylcarbamoyl)-7-(3,4-dehydropiperidyl-3)-benzo[b]thiophene 15.25 g (50 mmol) of 7-(N-benzyl-3,4 dehydropiperidyl-3)benzo[b]thiophene (which can be obtained as described in EP 0398413) is dissolved in 150 ml of dry tetrahydrofuran. The solution is cooled at −70 C. After adding 1.1 equivalent of butyllithium in hexane the reaction mixture is stirred for 30 minutes, after which a solution of methylisocyanate (6 ml) in tetrahydrofuran (50 ml) is added dropwise. The mixture is stirred for 30 minutes at −70 C., and overnight at room temperature. The reaction mixture is poured into 500 ml of water, and extracted with ethylacetate (3×200 ml). The combined organic layers are washed with water (2×200 ml), with brine (200 ml) dried and evaporated to dryness.

After purification by chromatografy (silicagel/ethylacetate:hexane=1:2). 2-(N-methylcarbamoyl)-7-(N-benzyl-3,4 dehydropiperidyl-3)-benzo[b]thiophene is obtained.

A solution of the so-obtained compound (9.6 g) in 1,2-dichloroethane (100 ml) is cooled to 0 C.

After adding 5.8 ml of 1-chloroethylchloroformate (53 mmol) the reaction mixture is heated to reflux temperature for two hours.

After evaporation of the benzylchloride, 100 ml of methanol is added and the reaction mixture is stirred at room temperature for 16 hours.

The solvent is evaporated and the residue is purified by chromatografy (silicagel/ethylacetate:methanol:ammonia=95:4.5:0.5. Yield 1.7 g of 2-(N-methylcarbamoyl)-7-(3,4-dehydropiperidyl-3)-benzo[b]thiophene. M.p. 173 C. (free base); 202 C. (fumarate).

The following compounds have also been prepared:

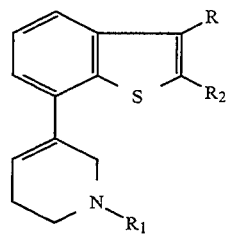

| EXAMPLE | R | $R_1$ | $R_2$ | melting point (C.) |
|---|---|---|---|---|
| II | H | H | —CON(CH$_3$)$_2$ | foam (fumarate) |
| III | H | H | —CH$_2$CON(CH$_3$)$_2$ | foam (fumarate) |
| IV | H | H | —CH$_2$NH—SO$_2$CH$_3$ | foam (free base) |
| V | H | H | —CH$_2$NH—COCH$_3$ | foam (fumarate) |
| VI | H | H | —CONH$_2$ | 292 (HCl) |
| VII | H | H | —SO$_2$NH$_2$ | >300 (HCl) |
| VIII | H | H | —SO$_2$NHCH$_3$ | 191 (HCl) |
| IX | CH$_3$ | H | —CONHCH$_3$ | 236 (HCl) |

The compounds of Examples II to V were obtained as a foam. These compounds have been identified by means of 'H-NMR spectra, among others of the protons in substituent $R_2$:

| Example | Spectrum of group $R_2$ |
|---|---|
| II | $\sigma$=3.24(3H, bs, N—CH$_3$); 3.08(3H, bs, N—CH$_3$) |
| III | $\sigma$=4.04(2H, s, —CH$_2$—); 3.09(3H, s, N—CH$_3$); 2.88(3H, s, N—CH$_3$) |
| IV | $\sigma$=4.45(2H, s, —CH$_2$); 2.90(3H, s, SO$_2$—CH$_3$) |
| V | $\sigma$=4.51(2H, d, —CH$_2$—; 8.59(1H, t, NH—CO); 1.89(3H, s, —CO—CH$_3$) | s = singlet
d = doublet
t = triplet
bs = broad singlet

We claim:

1. A 3,4-dehydropiperidine compound of the formula

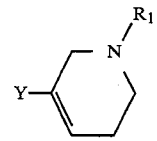

wherein
$R_1$ is a hydrogen atom or an alkyl group having 1-3 carbon atoms;
Y is a group of the formula 2

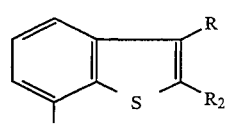

wherein
$R_2$ is a group of the formula —(CH$_2$)$_n$—C(=X)—NR$_3$R$_4$, —(CH$_2$)$_n$—SO$_2$—NR$_3$R$_4$, —(CH$_2$)$_n$—NR$_5$—C(=X)—R$_6$ or —(CH$_2$)$_n$—NR$_5$—SO$_2$—R$_6$, wherein R$_3$, R$_4$ and R$_5$ independent of each other represent hydrogen or alkyl (1-3C), R$_6$ is alkyl (1-3C), X represents O or S; and n is 0-4; R is hydrogen or alkyl (1-3C),
and a pharmaceutically acid addition salt thereof.

2. A pharmaceutical composition which comprises a 3,4-dehydropiperidine compound defined in claim 1 and a carrier.

3. A method of treating migraine in a human patient, said method comprising administering an antimigraine effective amount of a compound as claimed in claim 1 to the patient.

* * * * *